United States Patent
Wagner et al.

(10) Patent No.: US 9,428,616 B2
(45) Date of Patent: *Aug. 30, 2016

(54) LOW VISCOSITY POLYORGANOSILOXANES COMPRISING QUATERNARY AMMONIUM GROUPS, METHODS FOR THE PRODUCTION AND THE USE THEREOF

(71) Applicant: Momentive Performance Materials GmbH, Leverkusen (DE)

(72) Inventors: Roland Wagner, Bonn (DE); Karl-Heinz Stachulla, Leverkusen (DE); Karl-Heinz Sockel, Leverkusen (DE); Sigfredo Gonzales, Danbury, CT (US); Anne Dussaud, Tarrytown, NY (US)

(73) Assignee: Momentive Performance Materials GmbH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/387,599

(22) PCT Filed: Mar. 26, 2013

(86) PCT No.: PCT/US2013/033806
§ 371 (c)(1),
(2) Date: Sep. 24, 2014

(87) PCT Pub. No.: WO2013/148629
PCT Pub. Date: Oct. 3, 2013

(65) Prior Publication Data
US 2015/0299400 A1 Oct. 22, 2015

Related U.S. Application Data

(60) Provisional application No. 61/617,180, filed on Mar. 29, 2012.

(51) Int. Cl.
| | |
|---|---|
| *A61K 8/898* | (2006.01) |
| *C08G 77/26* | (2006.01) |
| *C08L 83/10* | (2006.01) |
| *D06M 13/46* | (2006.01) |
| *D06M 15/643* | (2006.01) |
| *A61Q 5/12* | (2006.01) |
| *A61Q 5/02* | (2006.01) |
| *A61Q 5/06* | (2006.01) |
| *C08G 77/06* | (2006.01) |
| *C09D 183/08* | (2006.01) |
| *C11D 3/00* | (2006.01) |
| *C11D 3/37* | (2006.01) |
| *C11D 11/00* | (2006.01) |
| *D06M 15/65* | (2006.01) |
| *C08G 77/14* | (2006.01) |
| *C08G 77/388* | (2006.01) |

(52) U.S. Cl.
CPC ............... *C08G 77/26* (2013.01); *A61K 8/898* (2013.01); *A61Q 5/02* (2013.01); *A61Q 5/06* (2013.01); *A61Q 5/12* (2013.01); *C08G 77/06* (2013.01); *C08L 83/10* (2013.01); *C09D 183/08* (2013.01); *C11D 3/001* (2013.01); *C11D 3/3742* (2013.01); *C11D 11/0017* (2013.01); *D06M 13/46* (2013.01); *D06M 15/643* (2013.01); *D06M 15/6433* (2013.01); *D06M 15/651* (2013.01); *C08G 77/14* (2013.01); *C08G 77/388* (2013.01)

(58) Field of Classification Search
None
See application file for complete search history.

(56) References Cited

U.S. PATENT DOCUMENTS

| | | | | |
|---|---|---|---|---|
| 4,833,225 | A * | 5/1989 | Schaefer | A61K 8/898 424/70.122 |
| 7,964,694 | B2 * | 6/2011 | Ferenz | A61K 8/898 424/122 |
| 2004/0048996 | A1 * | 3/2004 | Lange | A61K 8/898 528/10 |
| 2004/0138400 | A1 * | 7/2004 | Lange | A61K 8/898 528/38 |
| 2006/0163524 | A1 * | 7/2006 | Lange | A61K 8/416 252/8.63 |
| 2007/0106045 | A1 * | 5/2007 | Lange | A61K 8/046 528/29 |
| 2009/0142293 | A1 * | 6/2009 | Wagner | A61K 8/898 424/78.37 |
| 2011/0037012 | A1 * | 2/2011 | Wagner | C08G 77/388 252/8.63 |
| 2015/0037273 | A1 | 2/2015 | Wagner et al. | |
| 2015/0056155 | A1 | 2/2015 | Wagner et al. | |

FOREIGN PATENT DOCUMENTS

| | | |
|---|---|---|
| DE | 10 2005 036602 A1 | 2/2007 |
| WO | 2004/046452 A2 | 6/2004 |
| WO | 2004/090007 A2 | 10/2004 |
| WO | 2009/115412 A1 | 9/2009 |

* cited by examiner

Primary Examiner — Robert S Loewe
(74) Attorney, Agent, or Firm — Joseph S. Ostroff

(57) ABSTRACT

Low viscosity polyorganosiloxanes comprising a) at least one polyorganosiloxane group, b) at least one quaternary ammonium group, c) at least one terminal ester group, methods of the manufacture thereof and their use for the modification of surfaces of substrates.

19 Claims, No Drawings

LOW VISCOSITY POLYORGANOSILOXANES COMPRISING QUATERNARY AMMONIUM GROUPS, METHODS FOR THE PRODUCTION AND THE USE THEREOF

CROSS-REFERENCE TO RELATED APPLICATIONS

This application claims priority to U.S. Provisional Patent application Ser. No. 61/617,180 filed Mar. 29, 2012.

FIELD OF THE INVENTION

The present invention provides for a polyorganosiloxane having a low viscosity and comprising quaternary ammonium groups and terminal ester groups, methods for the production and use thereof.

BACKGROUND OF THE INVENTION

Silicone quats (silicones containing quaternary ammonium groups optionally containing polyorganosiloxane substituents) are known to be highly substantive. DE 3719086 describes the reaction of α,ω-diepoxides with tertiary amines in the presence of acids yielding α,ω-diquaternary siloxanes. They can be used for hair care purposes. DE 3719086 describes tetra alkyl derivatives as well as aromatic imidazolinium derivatives.

The reaction of α,ω-diepoxides with di-tertiary amines in the presence of acids yields polyloop polyquaternary polyorganosiloxanes (EP-A-282720). The advantage of these materials is an improved wash off resistance from hair.

The reaction of α,ω-diepoxides with dimethylamine in the presence of acids yields polyloop polyquaternary polyorganosiloxanes having one quat group between the siloxane blocks is disclosed in U.S. Pat. No. 6,730,766.

Polyquaternary imidazolinium derivates are described in U.S. Pat. No. 6,240,929. These cationic compounds possess an improved compatibility with anionic surfactants in cosmetic formulations.

The incorporation of alkylene oxide moieties in silicone quats is to further increase the hydrophilicity.

Silicone quats containing quat groups as well as polyethylene oxide moieties in side chains are described in U.S. Pat. No. 5,098,979, U.S. Pat. No. 5,153,294 and U.S. Pat. No. 5,166,297. The substantivity of the materials is relatively low.

Silicone based block copolymers containing quat functions that also include polyether moieties are described in WO 02/10257, WO 02/10259 and US 2002/0103094 A. The alkylene oxide structures are incorporated into the block copolymer as α,ω-difunctional moieties.

U.S. Pat. No. 6,242,554 describes α,ω-difunctional siloxane derivatives containing one polyether and one quat function separated from each other. The substantivity of these monoquats is insufficient.

U.S. Pat. No. 4,921,895 describes blends of polyethersiloxanes and quaternary ammonium groups containing siloxane block copolymers for textile finishing purposes. Here, the usage of the polyethersiloxane improves the finished goods and hydrophilicity.

US 2007/0286837, US 2007/0041929, US 2008/0292575 and CN 101198311 describe combinations between silicone quats having a siloxane chain length of greater than 200 D-units and a second silicone for hair conditioning purposes. One possible choice of the second silicone is the choice of silicone polyethers derived from ethylene oxide or propylene oxide or mixtures thereof. Specific structures are not given.

None of the above prior art disclosures describes a straight forward methodology for the preparation of low viscosity polyorganosiloxanes comprising quaternary ammonium groups. Low viscosity materials would make the incorporation of hydrophilicity improving substituents such as polyethers superfluous or redundant, thus reducing the system complexity.

SUMMARY OF THE INVENTION

The present invention provides for a low viscosity silicone (oligomerimeric or polymeric siloxane that is a homopolymer, copolymer or terpolymer) functionalized with quaternary ammonium groups and comprising one or more terminal ester groups as follows: a polyorganosiloxane compound comprising:
 a) at least one polyorganosiloxane group,
 b) at least one quaternary ammonium group,
 c) at least one terminal ester group.

The present invention further provides for a method of preparing the compounds of the present invention comprising the reaction of
 (i) at least one ditertiary diamine and/or secondary monoamine,
 (ii) at least one amino-alkylating compound, comprising at least one diepoxide, and
 (iii) at least one monofunctional organic acid,
 wherein at least one compound among compounds (i) and (ii) comprises polyorganosiloxane structural units.

DETAILED DESCRIPTION OF THE INVENTION

The present invention provides for low viscosity polyorganosiloxanes comprising quaternary ammonium groups, their manufacture and the use of the materials.

Surprisingly, polyorganosiloxanes comprising quaternary ammonium groups possessing a low viscosity is accomplished by the preparation of polyorganosiloxane compounds comprising quaternary ammonium groups and terminal ester groups. That is, in accordance with the present invention polyorganosiloxane compounds are provided comprising:
a) polyorganosiloxane groups,
b) quaternary ammonium groups,
c) terminal ester groups,
wherein in a preferably embodiment the molar ratio of the quaternary ammonium groups b) and the terminal ester groups c) is less than 100:20.

The polyorganosiloxane compounds according to the invention preferably are linear copolymer compounds that comprise the above functional groups a), b), with at least part of the terminal groups being terminal ester groups that result from the use of monofunctional organic acids as chain stoppers (formally [(A-B)$_x$-A]-type product (wherein x>1). However, depending on the stoichiometry of the reactants the polyorganosiloxane compounds according to the invention may also comprise compounds resulting from the reaction of a difunctional monomer with just one compound at each terminal thereof ([(A-B)$_x$-A]-type product (where x=1).

In a preferred embodiment the polyorganosiloxane compounds of the invention do not contain polyalkylene oxide groups except for polyalkylene oxide groups in the terminal ester groups, like in particular those of the general formulae:

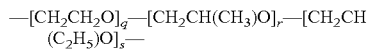

with
q=0 to 200,
r=0 to 200,
s=0 to 200
and q+r+s=1 to 600.

In a preferred embodiment of the polyorganosiloxane compounds according to the invention the at least one polyorganosiloxane groups are of the general formula:

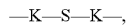

with

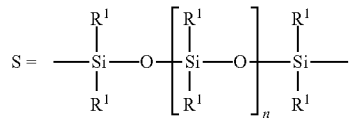

wherein $R^1$=$C_1$-$C_{22}$-alkyl, $C_1$-$C_{22}$-fluoralkyl or aryl,
n=0 to 1000, and these can be identical or different if several S Groups are present in the polyorganosiloxane compound, preferably for example n is for example in the range 0-200 or >200 to 1000;
K=is a bivalent or trivalent straight chain, cyclic and/or branched $C_2$-$C_{40}$ hydrocarbon residue which is optionally interrupted by —O—, —NH—, trivalent N, —$NR^1$—, —C(O)—, —C(S)—, and optionally substituted with —OH, wherein $R^1$ is defined as above, whereby the residues K can be identical or different from each other. In such group —K—S—K— the residue K is bound to the silicon atom of the residue S via a C—Si-bond.

In a preferred embodiment the polyorganosiloxane compounds according to the invention comprise at least one repeating unit comprising at least one quaternary ammonium group selected from the general formulas:

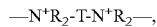

a saturated or unsaturated mono or diquaternary heterocycle of the formulae

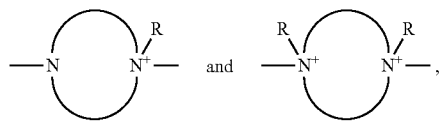

and
an aromatic ammonium heterocycle of the formula

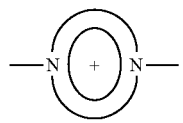

wherein R is selected from monovalent organic groups having up to 22 carbon atoms and optionally one or more heteroatoms, and wherein the free valencies at the nitrogen atoms are bound to carbon atoms, and T is selected from a divalent organic group having up to 20 carbon atoms and one or more hetero atoms. More specifically T is selected from the group of divalent hydrocarbon radicals comprising from one to twenty carbon atoms and as used herein for the definition of T the word comprising includes the group of hetero-atoms selected from the group of oxygen, sulfur, nitrogen, and phosporus. in the present invention the term quaternary ammonium group relates to a positively charged nitrogen atom that binds to 4 carbon atoms (formally known as $NR^4$+ groups).

In a preferred embodiment of the invention the terminal ester groups are selected from the group of:
—OC(O)—Z
—OS(O)$_2$—Z
—OS(O$_2$)O—Z
—OP(O)(O—Z)OH
—OP(O)(O—Z)$_2$ wherein Z is selected from monovalent organic residues having up to 40 carbon atoms, optionally comprising one or more hetero atoms. As will be explained in detail below these terminal ester groups result from the use of monofunctional organic acids, like carboxylic acids (—OC(O)—Z), sulfonic acids (—OS(O)$_2$—Z), sulfuric acid half ester (—OS(O$_2$)O—Z), phosphoric acid mono ester (—OP(O)(O—Z)OH), phosphoric acid diester (—OP(O)(O—Z)$_2$) in the reaction with diepoxides.

In a preferred embodiment the polyorganosiloxane compounds according to the invention have the general formula (I):

$$M-Y-[-(N^+R_2\text{-}T\text{-}N^+R_2)-Y-]_m\text{-}M \quad \text{(I), or}$$

$$M-Y-[-(N^+R_2)-Y-]_m\text{-}M \quad \text{(II)}$$

wherein:
m is an average value of 1 to 100, preferred 1 to 50, more preferred 1 to 20, even more preferred 1 to 10,
k is 0 or an average value of >0 to 50 preferred 1 to 20, more preferred 1 to 10,
M represents a terminal group, comprising terminal ester groups selected from
—OC(O)—Z
—OS(O)$_2$—Z
—OS(O$_2$)O—Z
—OP(O)(O—Z)OH
—OP(O)(O—Z)$_2$
wherein Z is as defined above,
$R^2$ is selected from hydrogen or R,
Y is T or a group of the formula:

—K—S—K—, each as defined above, with the proviso that at least one Y is a group of the formula —K—S—K— and T is a as defined above.

If amine groups are present in the polyorganosiloxane compounds according to the invention, they may be protonated for example with organic or inorganic acids. Such compounds are sometimes referred to as acid addition salts of the polyorganosiloxane compounds according to the invention.

In a preferred embodiment in the polyorganosiloxane compounds the molar ratio of the quaternary ammonium groups b) and the terminal ester groups c) is less than 100:30 and is most preferred less than 100:50. The ratio can be determined by $^{13}$C-NMR.

The polyorganosiloxane compounds according to the invention are manufactured preferably by a process, which comprises the reaction of
(i) at least one ditertiary diamine and/or secondary monoamine,
(ii) at least one amino-alkylating compound, comprising at least one diepoxide, and
(iii) at least one monofunctional organic acid,
wherein at least one compound among compounds (i) and (ii) comprises polyorganosiloxane structural units.

The present invention further relates to polyorganosiloxane compounds that are obtainable by the process according to the invention as described before.

A further embodiment of the present invention relates to polyorganosiloxane compositions, comprising:
A) at least one polyorganosiloxane compound according to the invention,
B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions according to the invention the weight ratio of compound A) to compound B) is preferably less than 90:10. Or with other words, the content of component B) is at least 10 weight percent. In a further preferred embodiment of the polyorganosiloxane compositions according to the invention in compound A) the molar ratio of the quaternary ammonium groups b) and the terminal ester groups c) is less than 100:20.

Both, the polysiloxanepolyorganosiloxane compounds or the polysiloxanepolyorganosiloxane compositions according to the invention preferably have a viscosity at 20° C. and a shear rate of 0.1 s$^{-1}$ (plate-plate system, plate diameter 40 mm, gap width 0.5 mm) of less than 100000 mPas (100 Pas).

The present invention further relates to aqueous emulsions comprising at least one polyorganosiloxane compound and/or at least one polyorganosiloxane composition as defined above or below. Such aqueous emulsions preferably comprise at least 30 weight percent, preferably at least 50 weight percent, still more preferably at least 80 weight percent water based on the total weight of the emulsions.

The present invention further relates to a method of surface treatment, comprising the step of applying the polyorganosiloxane compounds, the polyorganosiloxane compositions or the aqueous emulsions thereof as defined in any of the previous claims, to the surface of a substrate. Any method of applying it is conceivable, e.g. simple wetting, contacting, washing, dipping, spraying, brushing, spreading operations conventionally known in the art can be referred to.

In such method preferably one of a following compositions or formulations respectively are applied: cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

Further Preferred Embodiments of the Invention

In the polyorganosiloxane structural unit with the general formula S:

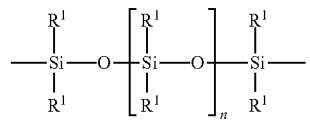

wherein $R^1$=$C_1$-$C_{22}$-alkyl, $C_1$-$C_{22}$-fluoroalkyl or aryl,
n=0 to 1000, preferred 0 to 500, more preferred 0 to 300, even more preferred 0 to 200, specifically 0 to 100 or in some instances >200 to 1000.

K (in the group —K—S—K—) is preferably a bivalent or trivalent straight chain, cyclical or branched $C_2$-$C_{20}$ hydrocarbon residue which is optionally interrupted by —O—, —NH—, trivalent N, —NR$^1$—, —C(O)—, —C(S)—, and optionally substituted with —OH.

In the polyorganosiloxanes of the invention the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be inter alia modified based upon the selection of acids used.

Quaternary ammonium groups as contained in the polyorganosiloxanes of the invention are usually generated by reacting the di-tertiary diamines with an alkylating agents, selected from in particular di-epoxides (sometimes referred to also as bis-epoxides) in the presence of mono carboxylic acids and difunctional dihalogen alkyl compounds.

$R^1$ is more preferred $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$ fluoroalkyl and aryl. Furthermore, $R^1$ is preferably $C_1$-$C_6$ alkyl, $C_1$-$C_6$ fluoroalkyl, more preferably $C_1$-$C_4$ fluoroalkyl, and phenyl. Even more preferably, $R^1$ is methyl, ethyl, trifluoropropyl and phenyl.

In the framework of the present invention, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl serve as examples.

In the framework of the present invention, the concept "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are presented as examples. In the framework of the present invention, "aryl" means unsubstituted or phenyl substituted once or several times with OH, F, Cl, CF$_3$, $C_1$-$C_6$ alkyl, $C_1$-$C_6$ alkoxy, $C_3$-$C_7$ cycloalkyl, $C_2$-$C_6$ alkenyl or phenyl. The expression can also mean naphthyl if need be.

In a preferred embodiment the polyorganosiloxane compounds are of the general formula (I):

wherein each group is as defined above.

Z in the groups M:
—OC(O)—Z
—OS(O)$_2$—Z
—OS(O$_2$)O—Z
—OP(O)(O—Z)OH
—OP(O)(O—Z)$_2$ is preferably is a straight chain, cyclic or branched saturated or unsaturated $C_1$-$C_{20}$, preferred $C_2$ to $C_{18}$, even more preferred-hydrocarbon radical, which can be interrupted by one or more —O—, or —C(O)— and substituted with —OH.

Preferred groups M are —OC(O)—Z resulting from normal carboxylic acids in particular with more than 10 carbon atoms like for example dodecanoic acid.

In a preferred embodiment of the invention the molar ratio of the polyorganosiloxane-containing repeating group —K—S—K— and the repeating group Y is between 100:0. As the case may require it may be also 100:1 and 1:100, preferred between 20:1 and 1:20, even more preferred between 10:1 and 1:10.

In the group —(N+R$_2$-T-N+R$_2$)— the groups R preferably represent a monovalent straight chain, cyclic or branched $C_1$-$C_{20}$ hydrocarbon radical, which can be interrupted by one or more —O—, —C(O)— and can be substituted by —OH, T preferably represent a divalent straight-chain, cyclic, or branched $C_1$-$C_{20}$ hydrocarbon radical, which can be interrupted by —O—, —C(O)— and can be substituted by hydroxyl.

The viscosities of the neat polymers according to this embodiment of the invention preferably are <100000 mPa·s, preferred <70000 mPa·s, more preferred <50000 mPa·s, even more preferred <20000 mPa·s, specifically <10000 mPa·s, more specifically <5.000 mPa·s but preferably does not fall short below 500 mPa·s determined at 20° C. and a shear rate of 0.1 s$^{-1}$. The molecular weight is between 10,000 and 100,000 g/mol measured as weight average Mw per GPC (gel permeation chromatography) and polystyrene as standard.

In a preferred embodiment of the invention, K is a divalent hydrocarbon radical having at least 4 carbon atoms, which contains one hydroxy group and can be interrupted by one oxygen atom.

Such groups include for example:

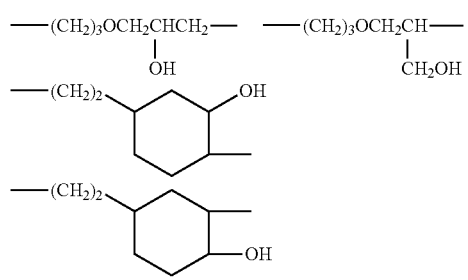

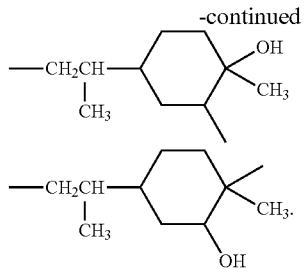

The polyorganosiloxane compounds of the invention are preferentially produced in a first embodiment via a method, in which first α,ωSi—H functionalized siloxanes of the general structure

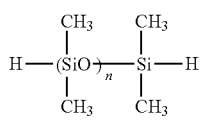

are converted, in the presence of a hydrosilylation catalyst and at temperatures of 50° to 150° C., with 1.0 to 1.5 mol, based upon SiH groups, of an alkenyl-epoxide, which has a terminal olefinic bond, wherein the alkenyl-epoxide contains at least 4 carbon atoms, and may additionally contain a non-cyclical ether group. Vinyl cyclohexene oxide and allylglycide ether are preferably used as epoxy-functional precursors for the production of epoxy functionalized siloxanes. The excess olefinic epoxide is then removed, if necessary.

The bisepoxide is preferably reacted with a mixture of one diamine, for example the preferred diamine of the formula

with R and T as defined above, or a secondary monoamine (that reacts two times to be quaternized).

Optionally in addition a α,ω carboxylic halogen alkyl acid ester may act as an alkylating agent. The reaction is preferably carried out in the presence of an organic acid at preferred 40° to 150° C., wherein the molar ratio of tertiary amino groups: Σ (epoxy groups+optional carboxylic haloacid ester groups) is for example ≤1:1, preferred ≤0.98:1, more preferred ≤0.9:1, even more preferred ≤0.7:1, specifically ≤0.5:1, the molar ratio of organic acid:epoxy groups ranges from 3:1 to 1:1, preferred from 2:1 to 1:1, more preferred from 1.5:1 to 1:1, even more preferred from 1.2:1 to 1:1, specifically is 1:1.

This means that i.e. either by reduction of the molar amount on tertiary amine and/or increase of the molar amount of organic acids low viscosity polyorganosiloxane compounds of the invention can be synthesized.

In a preferred variation of the embodiment, the species that contain the various amino groups may be added to the batch optionally together with the carboxylic haloacid ester derivatives, if necessary with the simultaneous addition of equimolar quantities of acid. It is also within the scope of the invention, however, to cause first the epoxy derivatives, the carboxylic haloacid ester derivatives, and the di-tertiary amines to react in the presence of a quantity of acid that is equivalent to that of the epoxy groups.

It is likewise possible to bring the carboxylic haloacid ester derivatives and the di-tertiary amines to react, forming hydrophilic blocks, and afterwards to add the epoxy derivatives, if necessary in the presence of a quantity of acid that is equivalent to that of the epoxy groups to the reaction mixture.

During the time in which the individual components are being added, the sequential distribution in the polymers being formed can be influenced.

It is further within the scope of the invention to cause several siloxane components of various chain lengths to react, while maintaining the desired overall stoichiometry. From this, there follows, e.g., the possibility of creating a desired siloxane chain length by using a single siloxane component or by the purposeful mixture of several siloxane components.

The quaternization and alkylation reactions are preferably run in polar organic solvents.

Suitable solvents are, for example organic solvents and water, including in particular mixtures of organic solvents and water, preferably polar organic solvents and water. Polar organic solvents include generally those comprising at least one heteroatome, like in particular oxygen, e.g., alcohols, especially methanol, ethanol, i-propanol and n-butanol; glycols, such as ethylene glycol, diethylene glycol, triethylene glycol, their methyl-, ethyl- and butyl ethers, 1,2-propylene glycol, dipropylene glycol, tripropylene glycol, their methyl-, ethyl- and butyl ethers and 1,3-propylene glycol; ketones, such as acetone and methylethylketone; esters, such as ethylacetate, butylacetate, methoxypropylacetate and 2-ethyl-hexylacetate; ethers, such as tetrahydrofuran; and nitro compounds, such as nitromethane.

It is preferred to run the reactions with a weight ratio of E polymer components: Σ (organic solvents+water) in a weight-range from 100:0 to 20:80, preferably 99.999:0.001 to 20:80, more preferred 95:5 to 20:80, still more preferred 95:5 to 50:50, even more preferred 95:5 to 60:40.

The amount on water in the composition of the reaction ranges in one embodiment from 0.1-0.5 wt. %, in an other embodiment preferably from 0.01-0.1 wt %; in an other embodiment the amount is in the range of 2-10 wt. % and preferably between 0.5-2 wt. %. In a preferred embodiment of the invention the desired amount of water is added separately. It is also possible to add the desired amount on water i.e. in form of solvent azeotropes or by the amount which is present in commercial grades.

The above described polyorganosiloxane compounds comprising quaternary ammonium functions and ester functions may contain individual molecules which contain quaternary ammonium functions and no ester functions, molecules which contain quaternary ammonium functions and ester functions as well as molecules which contain ester functions and no quaternary ammonium functions.

The above described polyorganosiloxane compounds comprising quaternary ammonium functions and ester functions are to be understood as mixtures of molecules comprising a certain averaged amount and ratio of both moieties.

Another less preferred embodiment of the invention relates to polyorganosiloxane compositions, comprising:
A) at least one polyorganosiloxane compound, as defined above,
B) at least one polyorganosiloxane compound, comprising at least one terminal ester group, different from compound A).

Such polyorganosiloxane compositions comprising quaternary ammonium functions and polyorganosiloxane compounds comprising ester functions are physically mixed in order to adjust the desired quat ($N^+$): ester ratio and the desired viscosity according to the invention. Both compounds are mixed in a ratio which fulfils the above outlined viscosity requirement according to the invention. The mixtures have a viscosities at 20° C. and a shear rate of 0.1 $s^{-1}$ of 500 to 100000 mPas, preferred 500 to 70000 mPas, more preferred 500 to 50000 mPa·s, even more preferred 500 to 20000 mPas, specifically 500 to 10000 mPas, more specifically 500 to 5000 mPa·s. The molecular weight is between 10,000 and 100,000 g/mol measured as weight average Mw per GPC (gel permeation chromatography) and polystyrene as standard.

The polyorganosiloxane compounds A) comprising quaternary ammonium functions are i.e. known from WO 02/10257. The synthesis of polyorganosiloxane compounds comprising ester functions is known from WO 2011/064255. They can i.e. be synthesized from the corresponding epoxy siloxanes by esterification with acids in the presence of a tertiary amine catalyst. The preferred polyorganosiloxane compounds B) comprising ester functions are α,ω-ester modified derivatives of the structure
M-(K—$S_n$—K)-M having siloxane chain length' in range from n=0 to 1000, preferred 0 to 500, more preferred 0 to 300, even more preferred 0 to 200, specifically 0 to 100. Alternatively, comb like derivatives comprising ester function as side groups in a difunctional siloxane unit (OSiMeR* with R*=carbon bound ester group)), and optionally terminal ester moieties ($O_{1/2}$ SiMe$_2$R* with R*=carbon bound ester group) of the same chain length range of n are also preferred. The number of ester-group-containing siloxy units is preferably from 1 to 500, preferred 1 to 250, more preferred 1 to 150, even more preferred 1 to 100, specifically 1 to 50, even more specific 1 to 25.

Preferred monofunctional organic acids yielding the esters are the ones forming the above mentioned counter ions. Preferred examples are $C_1$-$C_{30}$ carboxylic acids, for example C2, C3, C8 acids, $C_{10}$-$C_{18}$ carboxylic acids, for example C12, C14, C16 acids, saturated, unsaturated and hydroxyl functionalized C18 acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

The invention further relates to the use of the above-described polyorganosiloxane compounds in cosmetic formulations for skin and hair care, in polishing agents for treating and coating hard surfaces, in formulations for drying automobiles and other hard surfaces, for example following automatic washing, for finishing textiles and textile fibers, as separate softeners for use after textiles have been washed with non-ionogenic or anionic/non-ionogenic detergent formulations, as softeners in formulations for washing textiles that are based upon non-ionic or anionic/non-ionic surfactants, and as means for preventing or removing wrinkles in textiles.

The invention further relates to the use of the above-described polyorganosiloxane compounds as wash-resistant, hydrophilic softeners for use in the original finishing of textiles.

The invention further relates to compositions that contain at least one of the polyorganosiloxane compounds, together with at least one additional component that is commonly used in such a composition.

Below, a number of typical examples of these types of compositions are provided, in which the polyorganosiloxane compounds of the invention may be advantageously used: Typical adjuvants in these types of compositions are, e.g., those materials described in A. Domsch: Die kosmetischen Praeparate [Cosmetic Preparations] Vol. I and II, 4$^{th}$ Edition, Verl. fuer chem. Industrie [Publishers for the Chemical Industry], U. Ziolkowsky K G, Augsburg, and the International Cosmetic Ingredient Dictionary and Handbook 7$^{th}$ Ed. 1997 by J. A. Wenninger, G. N. McEwen Vol. 1-4 by The Cosmetic, Toiletry and Fragrance Association Washington D.C.

Anionic Shampoo

This formulation example is intended as a basic formulation. Anionic shampoos customarily contain, but are not limited to, the following components:

Alkylsulfates, alkylether sulfates, sodium lauryl sulfate, sodium lauryl ether sulfate, ammonium lauryl sulfate, ammonium lauryl-ether sulfate, TEA-lauryl sulfate, TEA-lauryl-ether sulfate, alkylbenzene sulfonates, α-olefinsulfonates, paraffin sulfonates, sulfosuccinates, N-acyltaurides, sulfate-glycerides, sulfatized alkanolamides, carboxylate salts, N-acyl-amino acid salts, silicones, etc.

| Components | wt-% |
|---|---|
| Ammonium lauryl sulphate | 10.00-30.00 |
| Ammonium lauryl-ether sulphate | 5.00-20.00 |
| Cocamidopropyl betaine | 0.00-15.00 |
| Lauramide DEA | 0.00-5.00 |
| Cocamide Mea | 0.00-5.00 |
| Dimethicone copolyol (dimethylsiloxane glycol copolymer) | 0.00-5.00 |
| Cyclopentasiloxane | 0.00-5.00 |
| Polyorganosiloxane compound of the invention | 0.50-5.00 |
| Polyquaternium-10 | 0.00-2.00 |
| Preservatives | 0.00-0.50 |
| Fragrance | 0.00-5.00 |
| Deionized water | q.s. 100% |
| Sodium chloride | q.s. |

Non-Ionic Shampoo

This formulation example is intended as a basic formulation. Non-ionic shampoos customarily contain, but are not limited to, the following components:

Monoalkanolamides, monoethanolamides, monoisopropanolamides, polyhydroxy derivatives, sucrose monolaurate, polyglycerine ether, amine oxides, polyethoxylated derivatives, sorbitol derivatives, silicones, etc.

| Components | Wt-% |
|---|---|
| Lauramide DEA | 10.00-30.00 |
| Lauramide oxide | 5.00-20.00 |
| Cocamide Mea | 0.00-5.00 |
| Dimethicone copolyol | 0.00-5.00 |
| Polyorganosiloxane compound of the invention | 0.50-5.00 |
| Preservatives | 0.00-0.50 |
| Fragrance | 0.00-5.00 |
| Deionized water | q.s. 100% |
| Sodium chloride | q.s. |

Amphoteric Shampoo

This formulation example is intended as a basic formulation. Formulations of this category customarily contain, but are not limited to, the following components:

N-alkyl-iminodipropionates, N-alkyl-iminopropionates, amino acids, amino acid derivatives, amido betaine, imidazolinium derivatives, sulfobetaines, sultaines, betaines, silicones, etc.

| Components | Wt-% |
|---|---|
| PEG-80-sorbitane laurate | 10.00-30.00 |
| Lauroamphoglycinate | 0.00-10.00 |
| Cocamidopropyl-hydroxysultain | 0.00-15.00 |
| PEG-150-distearate | 0.00-5.00 |
| Laurylether-13-carboxylate | 0.00-5.00 |
| Polyorganosiloxane compound of the invention | 0.50-5.00 |
| Fragrance | 0.00-5.00 |
| Deionized water | q.s. 100% |
| Sodium chloride | q.s. |

Cationic Shampoo

This formulation example is intended only as a basic formulation. Formulations of this category customarily contain, but are not limited to, the following components:

Bis-quaternary ammonium compounds, bis-(trialkylammonium acetyl)diamines, amido amines, ammonium alkylesters, silicones, etc.

| Components | Wt-% |
|---|---|
| Laurylether-13-carboxylate | 10.00-30.00 |
| Isopropylmyristate | 5.00-20.00 |
| Cocamidopropyl-betaine | 0.00-15.00 |
| Lauramide DEA | 0.00-5.00 |
| Cocamide MEA | 0.00-5.00 |
| Polyorganosiloxane compound specified in the invention | 0.50-5.00 |
| Preservatives | 0.00-0.50 |
| Fragrance | 0.00-5.00 |
| Deionized water | q.s. 100% |
| Sodium chloride | q.s. |

Setting Agents

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, etc.

| Components | Wt-% |
|---|---|
| Ceteareth-20 | 0.10-10.00 |
| Steareth-20 | 0.10-10.00 |
| Stearyl alcohol | 0.10-10.00 |
| Stearamidopropyl-dimethylamine | 0.00-10.00 |
| Dicetyldimonium-chloride | 0.00-10.00 |
| Polyorganosiloxane compound of the invention | 0.50-5.00 |
| Cyclopentasiloxane | 0.00-5.00 |
| Dimethicone | 0.00-5.00 |
| Preservatives | 0.00-0.50 |
| Fragrance | 0.00-5.00 |
| Deionized water | q.s. 100% |

"Clear Rinse-Off" Setting Agents

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, etc.

| Components | Wt-% |
|---|---|
| Glycerin | 0.10-10.00 |
| Cetrimonium chloride | 0.00-10.00 |
| Polyorganosiloxane compound of the invention | 0.50-5.00 |
| Hydroxyethyl cellulose | 0.00-5.00 |
| Preservatives | 0.00-0.50 |
| Fragrance | 0.00-5.00 |
| Deionized water | q.s. 100% |

Foam Setting Agents for Hair

This formulation example is intended as a basic formulation. Formulations of this category contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
|---|---|
| Polyorganosiloxane compound of the invention | 0.50-5.00 |
| Nonoxynol-15 | 0.00-2.00 |
| Nonoxynol-20 | 0.00-2.00 |
| Fragrance | 0.00-5.00 |
| Aerosol propellants | 0.00-20.00 |
| Preservatives | 0.00-0.50 |
| Deionized water | q.s. 100% |

Pump Spray (Setting Agents) for Hair

This formulation example is intended only as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | Wt-% |
|---|---|
| Polyorganosiloxane compound of the invention | 0.50-5.00 |
| Cyclomethicone | 0.00-80.00 |
| Ethanol | 0.00-80.00 |
| Preservatives | 0.00-0.50 |
| Fragrance | 0.00-5.00 |
| Deionized water | q.s. 100% |

Setting Agent Spray for Hair

This formulation example is intended as a basic formulation. Formulations of this category customarily contain, but are not limited to, the following components:

Fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
|---|---|
| Polyorganosiloxane compound of the invention | 0.50-5.00 |
| Cyclomethicone | 0.00-80.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 100% |

Gel Setting Agents for Hair

This formulation example is intended as a basic formulation. Formulations of this category customarily contain, but are not limited to, the following components: thickening agents, cellulose derivatives, acrylic acid derivatives, fixative polymers, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffin solvents, etc.

| Components | Wt-% |
|---|---|
| Polyorganosiloxane compound of the invention | 0.50-5.00 |
| Hydroxyethyl cellulose | 0.00-2.00 |
| Fragrance | 0.00-5.00 |
| Preservatives | 0.00-0.50 |
| Citric acid | 0.00-2.00 |
| Deionized water | q.s. 100% |

Rinse Off Conditioner

This formulation example is intended as a basic formulation. Formulations of this category customarily contain, but are not limited to, the following components: hydrocarbon based cationic conditioning agents, silicone based cationic conditioning agents, high melting fatty compounds, low melting oil like ester compounds, thickening agents, cellulose derivatives, fixative polymers, ethylene glycols, propylene glycols, glycol esters, glycerin, glycerin esters, monohydric alcohols, polyhydric alcohols, cationic polymers, nonionic and betain co-emulsifiers, silicones, complexing agents, solvents, fragrances, vitamins, solvents, etc.

| Components | Wt-% |
|---|---|
| Polyorganosiloxane compound of the invention | 0.50-10.00 |
| Cetyl Hydroxyethyl cellulose | 0.00-3.00 |
| Cetearyl alcohol | 0.00-3.00 |
| Glyceryl stearate and PEG-100 Stearate | 0.00-3.00 |
| Tetrasodium EDTA | 0.00-1.00 |
| Deionized water | q.s. 100% |

Styling Gel for Hair

This formulation example is intended as a basic formulation. Formulations of this category customarily contain, but are not limited to, the following components:

Fixative polymers, lacquers, acrylic acid derivatives, cellulose derivatives, vinyl derivatives, conditioning chemicals, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, etc.

| Components | % |
| --- | --- |
| Polyorganosiloxane compound of the invention | 0.50-5.00 |
| Fixing agents | 0.10-10.00 |
| Hydroxyethyl cellulose | 0.00-2.00 |
| Fragrance | 0.00-5.00 |
| Citric acid | 0.00-2.00 |
| Deionized water | q.s. 100% |

Styling Spray for Hair

This formulation example is intended as a basic formulation. Formulations of this category customarily contain, but are not limited to, the following components:

Fixative polymers, lacquers, vinyl derivatives, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
| --- | --- |
| Polyorganosiloxane compound of the invention | 0.50-5.00 |
| Cyclomethicone | 0.00-80.00 |
| Fixing agents | 0.10-10.00 |
| Ethanol | 0.00-50.00 |
| Aerosol propellants | 0.00-50.00 |
| Preservatives | 0.00-0.50 |
| Fragrance | 0.00-5.00 |
| Deionized water | q.s. 100% |

Pump Spray (Styling) for Hair

This formulation example is intended as a basic formulation. Formulations of this category customarily contain, but are not limited to, the following components:

Vinyl derivatives, fixative polymers, lacquers, fatty acids, fatty acid esters, ethoxylated fatty acids, ethoxylated fatty acid esters, fatty alcohols, ethoxylated fatty alcohols, glycols, glycol esters, glycerin, glycerin esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickening agents, silicones, solvents, ethanol, isopropanol, isoparaffin solvents, butane, propane, isobutane, CFC's fluorated aerosol propellants, dimethylether, compressed gases, etc.

| Components | Wt-% |
| --- | --- |
| Polyorganosiloxane compound of the invention | 0.50-5.00 |
| Fixing agents | 0.10-10.00 |
| Cyclomethicone | 0.00-80.00 |
| Ethanol | 0.00-50.00 |
| Preservatives | 0.00-0.50 |
| Fragrance | 0.00-5.00 |
| Deionized water | q.s. 100% |

The use of the polyorganosiloxane derivatives specified in the invention for applications in the hair care field produces favorable results with respect to strengthening, shine, fixing (hold), body, volume, moisture regulation, color retention, protection against environmental factors (UV, salt water, etc.), manageability, antistatic properties, ability to dye, etc.

EXAMPLES

The following examples are intended to describe the present invention in greater detail, without limiting its scope.

Example 1

Non Inventive

In a 500 ml three-necked flask, equipped with refluxing condenser, thermometer and mechanical stirrer, 150 g (58.7 mmol epoxy groups) of a silicone diepoxide of the structure

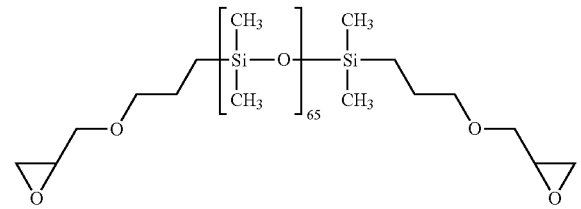

11.76 g (58.7 mmol) lauric acid, 5.06 g N,N,N',N'-tetramethylhexanediamine (58.7 mmol tert. amine), 31.3 g 2-propanol and 10.4 g distilled water are mixed at room temperature. The mixture is heated to reflux for 6 hours. Afterwards, the solvents are removed and the material analyzed by means of NMR and viscometry (see tab. 1). The dispersibility in water as well as the stability of the emulsion is poor.

Example 2

Inventive

In a 500 ml three-necked flask, equipped with refluxing condenser, thermometer and mechanical stirrer, 150 g (58.7 mmol epoxy groups) of a silicone diepoxide of the structure 11.76 g (58.7 mmol) lauric acid, 2.53 g N,N,N',N'-tetramethylhexanediamine (29.35 mmol tert. amine), 30.8 g 2-propanol and 10.3 g distilled water are mixed at room temperature. The mixture is heated to reflux for 6 hours. Afterwards, the solvents are removed and the material analyzed by means of NMR and viscometry (see tab. 1). The dispersibility in water as well as the stability of the emulsion is improved and on an acceptable level.

TABLE 1

| expl. # | solids % 120° C./30 min | viscosity mPas 20° C. 0.1 s−1 | ratio N+:ester** | dispersibility in water* |
|---|---|---|---|---|
| 1 | 98.0 | 112,000 | 100:18.7 | very poor |
| 2 | 98.3 | 8,300 | 100:68.5 | good |

*4 g of polyorganosiloxane material were added to 200 g of water and subjected to mixing with an Ultra Thurrax.
**$^{13}$C-NMR.

The data show that in the case of example 1 the non inventive reaction protocol yields a material which contains some ester functions but is too high in viscosity. As a consequence a very poor, uneven, lumpy and sticky dispersion in water is formed. Example 2 shows that reaction protocols according to the invention yield low viscosity materials which can be dispersed easily to small droplets having a sufficient stability.

Example 3

Inventive

The non inventive product of example 1 is mixed with a lauroyl ester modified siloxane of the structure

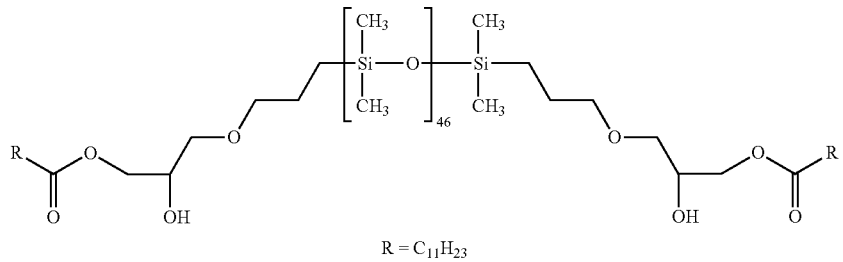

R = C$_{11}$H$_{23}$ which was synthesized from the corresponding epoxysiloxane, lauric acid and triethylamine (catalyst) in propylene glycol mono methyl ether according to WO 2011/064255.

The blending experiments are summarized in tab.2.

TABLE 2

| expl. # | ratio expl. 1:lauroyl ester | viscosity mPa · s 20° C. 0.1 s$^{-1}$ | dispersibility in water* |
|---|---|---|---|
| 3.1 | 100:0 | 112,000 | very poor |
| 3.2 | 90:10 | 52,700 | acceptable |
| 3.3 | 75:25 | 20,000 | good |

*4 g of polyorganosiloxane material were added to 200 g of water and subjected to mixing with an Ultra Thurrax.

The data for the examples 3.2 and 3.3 in tab.2 show that the physical blending of the non inventive material of example 1 with an ester modified siloxane yields mixtures which fall under the invention.

Example 4

Inventive

In a 500 ml three-necked flask, equipped with refluxing condenser, thermometer and mechanical stirrer, 97.4 g (9 mmol epoxy groups) of a silicone diepoxide of the structure

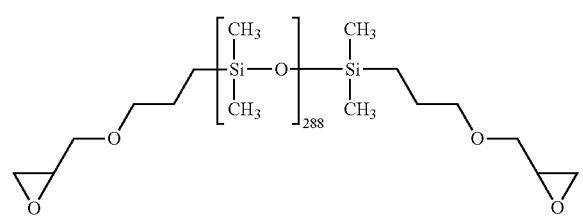

0.36 g (6 mmol) acetic acid, 0.52 g N,N,N',N'-tetramethylhexanediamine (6 mmol tert. amine), 96.5 g methoxy propanol and 1.97 g distilled water are mixed at room temperature. The mixture is heated to reflux for 4 hours. Afterwards, 0.18 g (3 mmol) acetic acid is added and the mixture maintained at reflux for additional 4 hours.

The solvents are removed. A polymeric material is obtained having a solids content of 95.68% (120° C./30 min) and a viscosity of 4300 mPa·s (20° C., 0.1 s$^{-1}$).

Example 5

Inventive

Conditioning performance was evaluated using a Diastron Combing Force apparatus. Single bleached tresses (4 g) from International Hair Importers were washed with 10% sodium lauryl sulphate solution and dried. The tresses were placed in a controlled humidity chamber at 50% (relative humidity RH) overnight before the baseline measurement of combing force, $F_b$.

The silicone polymer was dissolved in isopropanol to obtain solutions of 0.014 wt-% and 0.07 wt-%. About 2.8 g of isopropanol solution was distributed evenly on the hair tress with a pipette to obtain 100 ppm and 500 ppm silicone polymer on the hair, respectively. After overnight drying in a 50° C. oven, the tresses were placed in the controlled humidity chamber at 50% RH before the treated tress measurement of combing force, $F_t$. The dry combing force reduction corresponded to the value of $(F_b-F_t) \cdot 100/F_t$.

The results are summarized in tab. 3.

TABLE 3

|  |  | Concentration | |
| --- | --- | --- | --- |
|  |  | 500 ppm | 100 ppm |
| Silicone example 4 | $(F_b - F_t) \cdot 100/F_t$ | 58.8 | 36.9 |
| Commercially avalaible product )[3] | $(F_b - F_t) \cdot 100/F_t$ | 62.2 | −2.2 |

)[3] polyaminopropylmethylsiloxane

Tab. 3 shows that the inventive polyorganosiloxane provide a much better dry combing force reduction at low concentrations in the composition for hair treatment.

The invention claimed is:

1. A polyorganosiloxane compound comprising:
   a) at least one polyorganosiloxane group,
   b) at least one quaternary ammonium group,
   c) at least one terminal ester group, wherein the polyorganosiloxane compound is a linear copolymer compound which comprises the above functional groups (a) and (b), with at least part of the terminal groups being terminal ester groups (c) that result from the use of monofunctional organic acids as chain stoppers.

2. A polyorganosiloxane compound according to claim 1, wherein the molar ratio of the quaternary ammonium groups b) and the terminal ester groups c) is less than 100:20.

3. A polyorganosiloxane compound according to claim 1, which does not contain polyalkylene oxide groups except for the terminal ester groups.

4. A polyorganosiloxane compound according to claim 1, comprising at least one polyorganosiloxane group of the general formula:

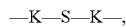
—K—S—K—, with

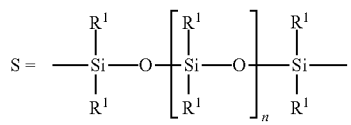

wherein $R^1 = C_1$-$C_{22}$-alkyl, $C_1$-$C_{22}$-fluoralkyl or aryl,
n=0 to 1000, and these can be identical or different if several S Groups are present in the polyorganosiloxane compound,
K=is a bivalent or trivalent straight chain, cyclic and/or branched $C_2$-$C_{40}$ hydrocarbon residue which is optionally interrupted by —O—, —NH—, trivalent N, —NR$^1$—, —C(O)—, —C(S)—, and optionally substituted with —OH, wherein $R^1$ is defined as above, whereby the residues K can be identical or different from each other.

5. A polyorganosiloxane compound according to claim 1, comprising at least one repeating unit comprising at least one quaternary ammonium group selected from the general formulas:

—N$^+$R$_2$—,

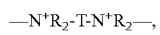
—N$^+$R$_2$-T-N$^+$R$_2$—, a saturated or unsaturated mono or diquaternary heterocycle of the formulae

and
an aromatic ammonium heterocycle of the formula

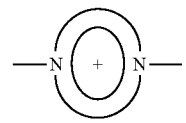

wherein R is selected from monovalent organic groups having up to 22 carbon atoms and optionally one or more heteroatoms, and wherein the free valencies at the nitrogen atoms are bound to carbon atoms, and T is selected from a divalent organic group having up to 20 carbon atoms and one or more hetero atoms.

6. A polyorganosiloxane compound according to claim 1, wherein the terminal ester groups are selected from the group of
   —OC(O)—Z
   —OS(O)$_2$—Z
   —OS(O$_2$)O—Z
   —OP(O)(O—Z)OH
   —OP(O)(O—Z)$_2$
   wherein Z is selected from monovalent organic residues having up to 40 carbon atoms, optionally comprising one or more hetero atoms.

7. A polyorganosiloxane compound according to claim 1 of the general formula (I):

$$M-Y-[-(N^+R_2\text{-}T\text{-}N^+R_2)-Y-]_m\text{-}M \quad (I), \text{ or}$$

$$M-Y-[-(N^+R_2)-Y-]_m\text{-}M \quad (II)$$

wherein:
m is an average value of 1 to 100,
k is 0 or an average value of >0 to 50,
M represents a terminal group, comprising terminal ester groups selected from
   —OC(O)—Z
   —OS(O)$_2$—Z
   —OS(O$_2$)O—Z
   —OP(O)(O—Z)OH
   —OP(O)(O—Z)$_2$
wherein Z is selected from monovalent organic residues having up to 40 carbon atoms, optionally comprising one or more hetero atoms,
$R^2$ is selected from hydrogen or R which is selected from monovalent organic groups having up to 22 carbon atoms and optionally one or more heteroatoms,
Y is T, or a group of the formula:

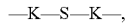
—K—S—K—, with

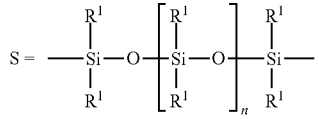

wherein $R^1=C_1$-$C_{22}$-alkyl, $C_1$-$C_{22}$-fluoralkyl or aryl, n=0 to 1000, and these can be identical or different if several S groups are present in the polyorganosiloxane compound, K=is a bivalent or trivalent straight chain, cyclic and/or branched $C_2$-$C_{40}$ hydrocarbon residue which is optionally interrupted by —O—, —NH—, trivalent N, —$NR^1$—, —C(O)—, —C(S)—, and optionally substituted with —OH, wherein $R^1$ is defined as above, whereby the residues K can be identical or different from each other with the proviso that at least one Y is a group of the formula —K—S—K— and T is selected from a divalent organic group having up to 20 carbon atoms and one or more hetero atoms.

8. A polyorganosiloxane compound according to claim 1, having protonated ammonium groups.

9. A process for the manufacture of polyorganosiloxane compounds according to claim 1, which comprises the reaction of
(i) at least one ditertiary diamine and/or secondary monoamine,
(ii) at least one amino-alkylating compound, comprising at least one diepoxide, and
(iii) at least one monofunctional organic acid,
wherein at least one compound among compounds (i) and (ii) comprises polyorganosiloxane structural units.

10. A polyorganosiloxane compound as prepared by the process of claim 9.

11. A polyorganosiloxane composition, comprising:
A) at least one polyorganosiloxane compound as defined in claim 1, and
B) at least one polyorganosiloxane compound, comprising at least one terminal ester group, different from compound A).

12. A polyorganosiloxane composition according to claim 11 wherein the weight ratio of compound A) to compound B) is less than 90:10.

13. A polyorganosiloxane composition according to claim 11 wherein in compound A) the molar ratio of the quaternary ammonium groups b) and the terminal ester groups c) is less than 100:20.

14. An aqueous emulsion comprising at least one polyorganosiloxane compound as defined in claim 1.

15. A method of surface treatment, comprising the step of applying the polyorganosiloxane compounds, as defined in claim 1, to the surface of a substrate.

16. A method of claim 15 wherein one of a following compositions or formulations respectively are applied: cosmetic formulations for skin and hair care, selected from Rinse-off and Leave-on conditioners, shampoos, styling gels, sprays, and pump sprays; formulations for polishing for the treatment and outfitting of hard surfaces; formulations for drying automobiles and other hard surfaces; formulations for initial outfitting of textiles and textile fibers; softener formulations comprising in addition non-ionogenic or anionic/non-ionogenic or cationic or betaine surfactants for application during or after washing textiles; laundry formulations for textile washes based upon non-ionic or anionic/non-ionic or cationic or betaine surfactants or formulations for preventing or reversing textile crumpling.

17. Polyorganosiloxane compounds according to claim 1, having a viscosity at 20° C. and a shear rate of 0.1 $s^{-1}$ below 100000 mPa.

18. A polyorganosiloxane compound consisting essentially of:
a) at least one polyorganosiloxane group,
b) at least one quaternary ammonium group, and
c) at least one terminal ester group, wherein the polyorganosiloxane compound is a linear copolymer compound which comprises the above functional groups (a) and (b), with at least part of the terminal groups being terminal ester groups (c) that result from the use of monofunctional organic acids as chain stoppers.

19. Polyorganosiloxane compounds according to claim 18, further consisting essentially of wherein the at least one quaternary ammonium group is

—$N^+R_2$-T-$N^+R_2$—, where T is selected from the group of divalent hydrocarbon radicals comprising from one to twenty carbon atoms and R is selected from monovalent organic groups having up to 22 carbon atoms and optionally one or more heteroatoms.

* * * * *